United States Patent
Lee et al.

(10) Patent No.: US 10,713,822 B2
(45) Date of Patent: Jul. 14, 2020

(54) TOMOGRAPHIC IMAGING APPARATUS, METHOD OF CONTROLLING THE SAME, AND COMPUTER PROGRAM PRODUCT

(71) Applicant: Samsung Electronics Co., Ltd., Suwon-si (KR)

(72) Inventors: Sang-min Lee, Incheon (KR); Dong-uk Kang, Hwaseong-si (KR); Do-il Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 99 days.

(21) Appl. No.: 16/147,378

(22) Filed: Sep. 28, 2018

(65) Prior Publication Data
US 2019/0213759 A1    Jul. 11, 2019

(30) Foreign Application Priority Data
Jan. 11, 2018    (KR) .................. 10-2018-0003973

(51) Int. Cl.
*A61B 5/00*        (2006.01)
*A61B 6/00*        (2006.01)
(Continued)

(52) U.S. Cl.
CPC .............. *G06T 11/003* (2013.01); *A61B 6/02* (2013.01); *A61B 6/42* (2013.01); *A61B 6/4241* (2013.01); *A61B 6/4291* (2013.01); *A61B 6/482* (2013.01); *G01J 1/44* (2013.01); *G01J 1/46* (2013.01); *G01N 23/046* (2013.01); *G01T 1/1647* (2013.01); *G01T 1/17* (2013.01); *G01T 1/2018* (2013.01); *G01T 1/247* (2013.01); *G01T 1/2985* (2013.01); *H04N 5/32* (2013.01);
(Continued)

(58) Field of Classification Search
CPC ................ G01J 1/00; H04N 5/00; A61B 6/00
USPC ....................................................... 382/131
See application file for complete search history.

(56) References Cited

U.S. PATENT DOCUMENTS 5,943,388 A    8/1999    Tumer
7,528,377 B2 *  5/2009    El-Hanany ............ G01T 1/2928
                                            250/370.01
(Continued)

FOREIGN PATENT DOCUMENTS

WO        2017/009736 A1    1/2017

OTHER PUBLICATIONS

European Search Report dated Mar. 22, 2019 in connection with European Patent Application No. 18 18 9913, 9 pages.

*Primary Examiner* — Abolfazl Tabatabai

(57) ABSTRACT

A tomographic imaging apparatus includes an X-ray detector comprising a plurality of dual mode pixels and configured to detect radiation that has passed through an object, and at least one processor configured to obtain scan data from the X-ray detector, and control each pixel of the plurality of dual mode pixels to operate in one of a first mode and a second mode, wherein each pixel of the plurality of dual mode pixels includes a sensor configured to generate a scan signal by converting incident radiation into an electric signal, a first signal path circuit configured to transmit the scan signal in the first mode, a second signal path circuit configured to transmit the scan signal in the second mode, and a photon counter configured to count photons from the scan signal transmitted through one of the first and second signal path circuits.

20 Claims, 14 Drawing Sheets

(51) Int. Cl.
*G06T 11/00* (2006.01)
*G01T 1/164* (2006.01)
*G01T 1/24* (2006.01)
*H04N 5/3745* (2011.01)
*H04N 5/32* (2006.01)
*G01T 1/20* (2006.01)
*G01T 1/17* (2006.01)
*A61B 6/02* (2006.01)
*G01J 1/44* (2006.01)
*G01T 1/29* (2006.01)
*G01J 1/46* (2006.01)
*G01N 23/046* (2018.01)
*G01V 5/00* (2006.01)

(52) U.S. Cl.
CPC ....... *H04N 5/3745* (2013.01); *H04N 5/37455* (2013.01); *G01J 2001/442* (2013.01); *G01N 2223/423* (2013.01); *G01N 2223/501* (2013.01); *G01T 1/171* (2013.01); *G01V 5/005* (2013.01); *G06T 2207/10116* (2013.01)

(56) References Cited

U.S. PATENT DOCUMENTS

| | | | |
|---|---|---|---|
| 8,816,290 B2 * | 8/2014 | Hamlin | G01T 1/17 250/370.08 |
| 2004/0239377 A1 | 12/2004 | Tumer et al. | |
| 2006/0056576 A1 | 3/2006 | Hoffman et al. | |
| 2007/0076848 A1 | 4/2007 | Walter et al. | |
| 2008/0099689 A1 | 5/2008 | Nygard et al. | |
| 2009/0121142 A1 | 5/2009 | Heismann et al. | |
| 2009/0128216 A1 | 5/2009 | Rao et al. | |
| 2010/0187432 A1 | 7/2010 | Herrmann et al. | |
| 2010/0207027 A1 | 8/2010 | Marks et al. | |
| 2017/0212253 A1 | 7/2017 | Fu et al. | |

* cited by examiner

TOMOGRAPHIC IMAGING APPARATUS, METHOD OF CONTROLLING THE SAME, AND COMPUTER PROGRAM PRODUCT

CROSS-REFERENCE TO RELATED APPLICATION(S) AND CLAIM OF PRIORITY

This application is based on and claims priority under 35 U.S.C. § 119 to Korean Patent Application No. 10-2018-0003973 filed on Jan. 11, 2018 in the Korean Intellectual Property Office, the disclosure of which is incorporated by reference herein in its entirety.

BACKGROUND

1. Field

The disclosure relates to a tomographic imaging apparatus, a method of controlling the tomographic imaging apparatus, and a computer program product including a computer-readable recording medium having recorded thereon a program which performs the method.

2. Description of Related Art

A medical imaging apparatus is an apparatus for obtaining an image of an internal structure of an object. The medical imaging apparatus is a non-invasive examination apparatus which images, processes, and shows, to a user, structural details, internal tissue, and fluid flow of a human body. The user, such as a doctor, may diagnose a health state and a disease of a patient by using a medical image that is output from the medical imaging apparatus.

An example of an apparatus for imaging an object by irradiating a patient with X-rays includes a computed tomography (CT) apparatus. The CT apparatus is a type of a medical imaging apparatus or a tomographic imaging apparatus. The CT apparatus is widely used to precisely diagnose a disease because the CT apparatus may provide a cross-sectional image of an object and render internal structures (for example, organs such as a kidney and a lung) of the object in such a manner that they do not overlap with each other, unlike general X-ray apparatuses.

In order to accurately image a patient for diagnosis, an energy level and intensity of detected radiation need to be measured. In this regard, a photon counting detector (PCD) can be used to detect radiation. The PCD requires a high counting speed and energy spectrum accuracy. The high counting speed is required to count photons at a certain location for a short period of time when an X-ray generator rotates at a high speed. The energy spectrum accuracy is required to distinguish intensity of photons incident on the PCD. However, it can be difficult to simultaneously obtain a high counting speed and energy spectrum accuracy.

SUMMARY

Certain embodiments according this disclosure provide a tomographic imaging apparatus using a photon counting detector (PCD) in which a high counting speed and energy spectrum accuracy are simultaneously obtained, a method of controlling the tomographic imaging apparatus, and a computer program product for same.

Various embodiments according to this disclosure comprise an apparatus and a method for increasing a photon counting speed while reducing a dead time of photon counting by complementing advantages of using an energy spectrum method having excellent energy resolution and using a high speed counting method having a high photon counting speed in a photon counting detector (PCD).

Additional aspects will be set forth in part in the description which follows and, in part, will be apparent from the description, or may be learned by practice of the presented embodiments.

In accordance with an aspect of the disclosure, a tomographic imaging apparatus includes an X-ray detector including a plurality of dual mode pixels and configured to detect radiation that has passed through an object; and at least one processor configured to obtain scan data from the X-ray detector, and control each of the plurality of dual mode pixels to operate in one of a first mode and a second mode, wherein each of the plurality of dual mode pixels includes a sensor configured to generate a scan signal by converting incident radiation into an electric signal, a first signal path circuit configured to transmit the scan signal in the first mode, a second signal path circuit configured to transmit the scan signal in the second mode, and a photon counter configured to count photons from the scan signal transmitted through one of the first and second signal path circuits, wherein a minimum time interval of transmitting the scan signal of the second signal path circuit is smaller than that of the first signal path circuit.

The first signal path circuit may include a first preamplifier configured to amplify the scan signal; and a pulse shaper configured to shape a waveform of the scan signal.

The second signal path circuit may include a second preamplifier configured to amplify the scan signal; and a reset circuit configured to reset input and output levels of the second preamplifier when the output level of the second preamplifier exceeds a first level.

The at least one processor may be further configured to generate a model selection signal for selecting one of the first mode and the second mode and output the mode selection signal to the X-ray detector, wherein each of the plurality of dual mode pixels may further include: a first switch configured to transmit, to one of the first signal path circuit and the second signal path circuit, the scan signal output from the sensor, according to the mode selection signal and a second switch configured to connect, to one of the first signal path circuit and the second signal path circuit, an input terminal of the photon counter, according to the mode selection signal.

The X-ray detector may include a plurality of binning pixels including a plurality of sub-pixels, wherein the plurality of dual mode pixels may be grouped as sub-pixels to be included in the plurality of binning pixels, and the at least one processor may be further configured to control at least one first dual mode pixel in each of the plurality of binning pixels to operate in the first mode and control remaining at least one second dual mode pixel excluding the at least one first dual mode pixel to operate in the second mode.

The X-ray detector may further include an anti-scatter grid provided on the plurality of dual mode pixels, and the at least one processor may be further configured to control, from among the plurality of dual mode pixels, dual mode pixels provided around a frame of the anti-scatter grid to operate in the first mode and control remaining dual mode pixels excluding the dual mode pixels provided around the frame to operate in the second mode.

The at least one processor may be further configured to control, from among the plurality of dual mode pixels, dual mode pixels provided at an outer region to operate in the first mode and control remaining dual mode pixels excluding the dual mode pixels provided at the outer region to operate in the second mode.

The tomographic imaging apparatus may further include an input device configured to receive a first control signal, wherein the at least one processor may be further configured to control a mode of each of the plurality of dual mode pixels of the X-ray detector based on the first control signal.

The tomographic imaging apparatus may further include an X-ray generator configured to generate and output X-rays, wherein the at least one processor may be further configured to control a mode of each of the plurality of dual mode pixels based on at least one of a tube voltage and a tube current of the X-ray generator.

The at least one processor may control a mode of each of the plurality of dual mode pixels based on an imaging protocol.

The photon counter may include a plurality of comparators configured to compare the scan signal transmitted via one of the first signal path circuit and the second signal path circuit with a threshold voltage, and a plurality of counters respectively configured to count output signals of the plurality of comparators.

In accordance with another aspect of the disclosure, a method of controlling a tomographic imaging apparatus, wherein an X-ray detector of the tomographic imaging apparatus includes a plurality of dual mode pixels operating in a first mode or a second mode, wherein each of the plurality of dual mode pixels includes a first signal path circuit configured to transmit a scan signal output from a sensor in the first mode, a second signal path circuit configured to transmit the scan signal in the second mode, and a photon counter configured to count photons from the scan signal, the method includes: controlling each of the plurality of dual mode pixels to operate in one of the first mode and the second mode, and obtaining scan data output from the X-ray detector, wherein a minimum time interval of transmitting the scan signal of the second signal path circuit is smaller than that of the first signal path circuit.

In accordance with another aspect of the disclosure, a computer program product includes a computer-readable recording medium having recorded thereon a program which, when executed by a computer, performs the method.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
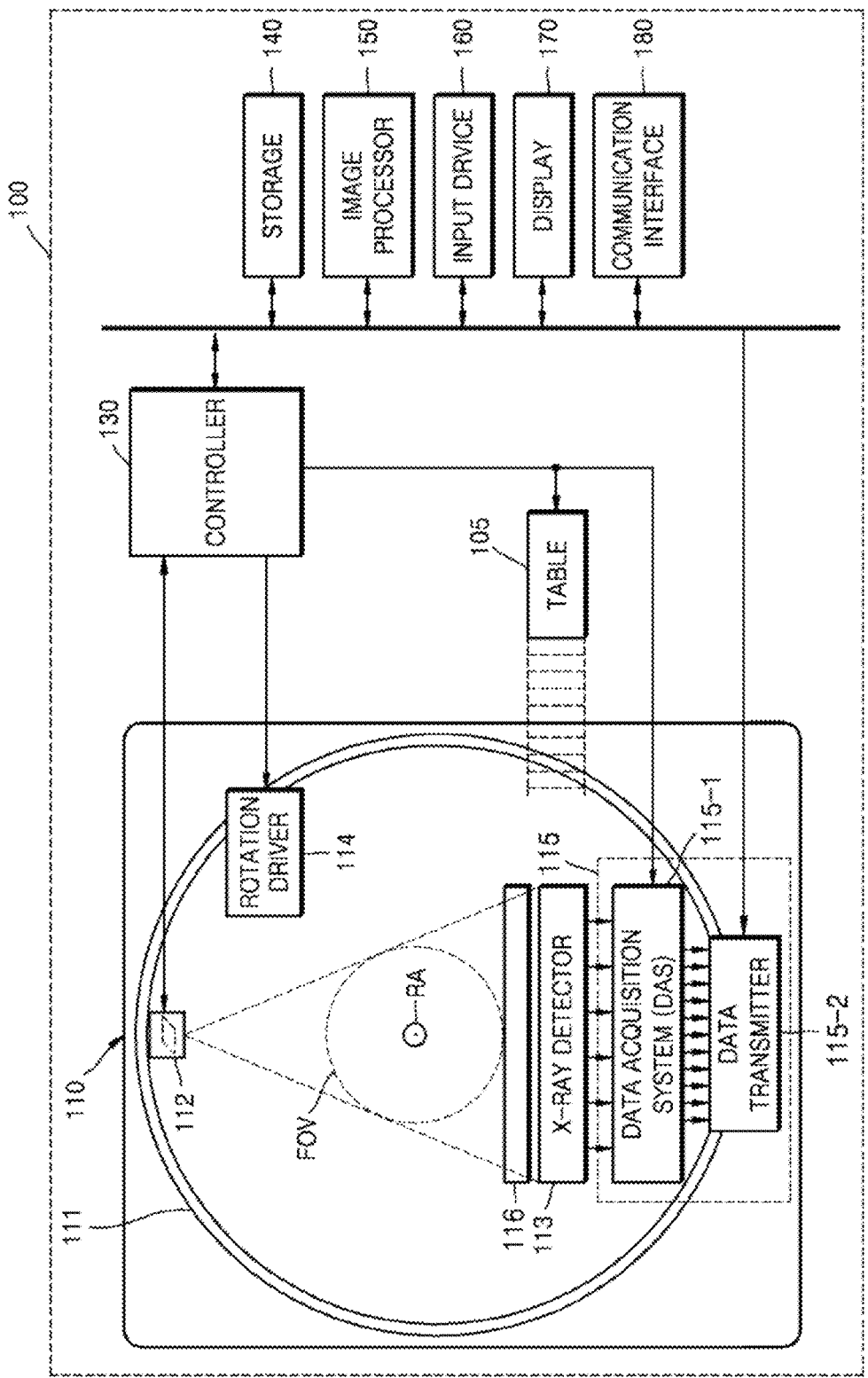
FIG. 1 illustrates structural aspects of a computed tomography (CT) system according to certain embodiments.

FIGS. 1 through 14, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The principles of the present disclosure are explained and embodiments are disclosed so that the scope of the present disclosure is clarified and one of ordinary skill in the art to which the present disclosure pertains may implement embodiments according to the present disclosure. The disclosed embodiments may have various forms.

Throughout the specification, like reference numerals or characters refer to like elements. In the present specification, all elements of embodiments are not explained, but general matters in the technical field of the present disclosure or redundant matters between embodiments will not be described. Terms 'module' or 'unit' used herein may be implemented using at least one or a combination from among software, hardware, or firmware, and, according to embodiments, a plurality of 'module' or 'unit' may be implemented using a single element, or a single 'module' or 'unit' may be implemented using a plurality of units or elements. The operational principle of the present disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MM) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

FIG. 1 illustrates a structure of a CT system 100 according to some embodiments.

As shown in the non-limiting example of FIG. 1, CT system 100 may include a gantry 110, a table 105, a controller 130, a storage 140, an image processor 150, an input device 160, a display 170, and a communication interface 180.

The gantry 110 may include a rotating frame 111, an X-ray generator 112, an X-ray detector 113, a rotation driver 114, and a readout device 115.

The rotating frame 111 may receive a driving signal from the rotation driver 114 and rotate around a rotation axis (RA).

An anti-scatter grid 116 may be disposed between an object and the X-ray detector 113 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays.

The CT system 100 may be implemented as a single-source CT system including one X-ray generator 112 and one X-ray detector 113, or as a dual-source CT system including two X-ray generators 112 and two X-ray detectors 113.

The X-ray detector 113 detects radiation that has passed through the object. For example, the X-ray detector 113 may detect radiation by using a scintillator, a photon counting detector, etc.

Methods of driving the X-ray generator 112 and the X-ray detector 113 may vary depending on scan modes used for scanning of the object. The scan modes are classified into an axial scan mode and a helical scan mode, according to a path along which the X-ray detector 113 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store a program for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 113 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 113, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 113 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

The image processor 150 may perform pre-processing, such as a process of correcting sensitivity irregularity between channels, a process of correcting a rapid decrease of signal strength, or a process of correcting signal loss due to an X-ray absorbing material, on the signal obtained by the readout device 115.

According to embodiments, the image processor 150 may perform some or all of the processes for reconstructing a tomography image, to thereby generate the tomography data. According to certain embodiments, the tomography data may be in the form of data that has undergone back-projection, or in the form of a tomography image. According to embodiments, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The input device 160 receives control signals, data, etc., from a user. The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

According to various embodiments, the CT system 100 may use contrast media during a CT scan, and may be implemented as a device connected to other equipment.

Figure 2:
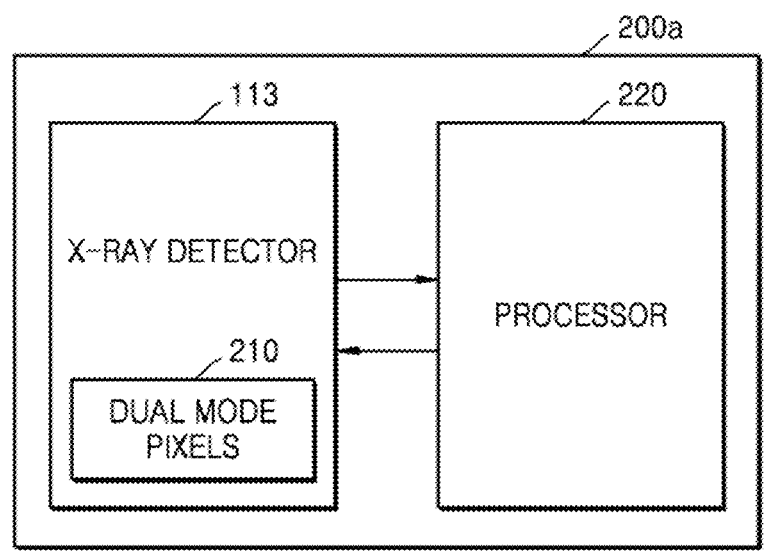
FIG. 2 illustrates, in block diagram format, a tomographic imaging apparatus according to some embodiments.

FIG. 2 illustrates, in block diagram format, a tomographic imaging apparatus 200a according to various embodiments.

The tomographic imaging apparatus 200a according to some embodiments may be embodied in a form of any electronic device detecting photons. For example, the tomographic imaging apparatus 200a according to certain embodiments may be embodied in a form of a computed tomography (CT) system, an optical coherence tomography (OCT) apparatus, a positron emission tomography (PET)-CT apparatus, or a single photon emission computed tomography (SPECT) apparatus.

Also, the tomographic imaging apparatus 200a according to various embodiments may be embodied as part of the CT system 100 of FIG. 1.

According to certain embodiments, a CT system may include a radiation source emitting poly-energetic ionizing photons, and a detector that detected photons passed through a target object may reconstruct a tomographic image by generating an electric signal of a current or voltage and classifying the electric signal according to energy size. The CT system includes a scintillator converting X-rays into visible light, and a photodiode converting the visible light into an electric signal. The CT system may convert incident radiation into light and then convert the light into an electric signal to obtain a scan signal indicating an attenuation degree of photons that passed through an object. Also, the CT system may integrate the obtained scan signal for a certain period of time to obtain scan data. However, according to such a method of integrating the scan signal for the certain period of time, an energy size of the incident radiation may not be accurately identified. In this regard, tomographic imaging apparatus 200a uses a detector using a method of counting photons passing through an object, i.e., a PCD. The PCD is able to directly count entered photons by using a semiconductor material that converts photons directly into electric signals. Such a PCD using a direct converting method includes a preamplifier that amplifies a pulse having a peak amplitude or height according to an energy size, a pulse shaper that reshapes the pulse according to the energy size, a discriminator that discriminates energy by comparing at least one energy threshold value and a pulse height, and a counter that counts the number of times when the pulse height exceeds the at least one energy threshold value.

Radiation flux used in the tomographic imaging apparatus 200a is about $10^8$ to $10^9$ photons/sec*$mm^2$, wherein a photon counting speed is important in counting photons at a certain location for a short period of time while the tomographic imaging apparatus 200a rotates the X-ray generator 112 at a high speed, and energy spectrum accuracy is an important factor in distinguishing intensities of photons incident on the X-ray detector 113. Energy precision is enhanced when a pulse shaping time of a pulse shaper is increased, and the energy precision is reduced when the pulse shaping time is decreased to increase a speed. However, a pulse shaper may be required in order to increase the energy spectrum accuracy, but the pulse shaper lowers a photon counting speed. Accordingly, a high counting speed and energy spectrum accuracy are to a certain extent, mutually exclusive and thus difficult to simultaneously obtain. An energy level of a pulse signal generated from an amplifier may be accurately determined as the pulse signal passes through the pulse shaper, but a photon counting speed may be decreased as a dead time, in which a signal input while a pulse is being shaped is lost without being processed, occurs. When the pulse shaper is removed to increase the photon counting speed and a method of resetting a received signal equal to or higher than a threshold value is used, the photon counting speed may be increased as a decay time of an output signal of the pulse shaper having a Gaussian pulse shape is reduced. However, a signal equal to or lower than a threshold value can have a long decay time, and energy precision may be low compared to a pulse shaper where low-band noise and high-band noise are removed.

The tomographic imaging apparatus 200a according to some embodiments includes the X-ray detector 113 and a processor 220. The X-ray detector 113 includes a plurality of dual mode pixels 210.

Referring to the non-limiting example of FIG. 2, X-ray detector 113 detects X-rays that passed through an object emitted from the X-ray generator 112 to generate and output scan data. The X-ray detector 113 according to certain embodiments may include a plurality of pixels for detecting the X-rays. The plurality of pixels may be arranged in a 2-dimensional (2D) array.

According to various embodiments, some or all of the plurality of pixels of the X-ray detector 113 may be embodied as the dual mode pixels 210.

According to some embodiments, the plurality of pixels may include a sensor generating a scan signal corresponding to radiation that passed through an object, a preamplifier amplifying the scan signal, and a photon counter counting photons from the scan signal generated by the sensor. In other words, the plurality of pixels may be pixels using a PCD.

Dual mode pixels 210 include a first signal path circuit and a second signal path circuit, and transmit the scan signal to the photon counter through one of the first and second signal path circuits. A minimum time interval of transmitting the scan signal of the second signal path circuit is smaller than that of the first signal path circuit. In other words, the second signal path circuit transmits the scan signal faster than the first signal path circuit.

According to various embodiments, processor 220 receives the scan data obtained by the X-ray detector 113. The scan data may be raw data, such as projection data or a sinogram. Also, the processor 220 controls overall operations of the X-ray detector 113, generates a control signal for controlling a mode of the dual mode pixels 210, and outputs the control signal to the X-ray detector 113. For example, the processor 220 may generate and output a mode selection signal to control the dual mode pixels 210 to operate in a first mode or a second mode. The processor 220 may reconstruct a tomographic image by using the obtained scan data. The processor 220 may reconstruct a tomographic image from raw data by using a technique, such as filtered back-projection.

According to certain embodiments, the mode selection signal may be output from the processor 220 to the X-ray detector 113 through at least one of or a combination of the DAS 115-1 and the data transmitter 115-2.

According to certain other embodiments, a separate signal wire for transmitting the mode selection signal may be provided between the processor 220 and the X-ray detector 113.

According to various embodiments, X-ray detector 113 of FIG. 2 corresponds to X-ray detector 113 of FIG. 1, and processor 220 of FIG. 2 may correspond to controller 130, or image processor 150 of FIG. 1, or a combination thereof.

Figure 3A:
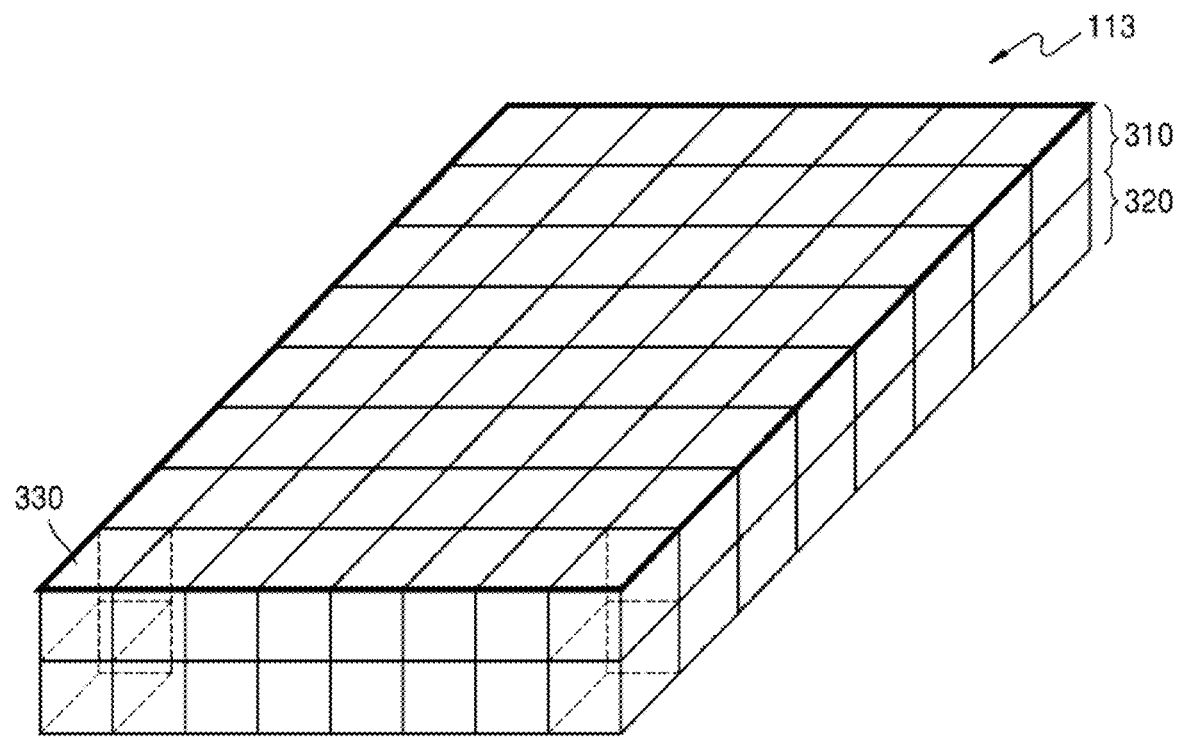
FIG. 3A illustrates an X-ray detector according to certain embodiments.

FIG. 3A illustrates an X-ray detector 113 according to some embodiments.

Referring to the non-limiting example of FIG. 3, X-ray detector 113 according to certain embodiments is a counting detector in which radiation is detected via a direct method of converting incident ration directly to charges. In detail, the X-ray detector 113 is a PCD that converts incident photons to an electric signal, and counts the number of photons by using the electric signal. Also, the X-ray detector 113 according to various embodiments may have a structure capable of multiple energy measurements.

According to some embodiments, X-ray detector 113 for multiple energy measurements classifies photons into a plurality of energy bands based on energy sizes, and restores a medical image by using the number of photons classified into the plurality of energy bands. In detail, an X-ray detector 113 according to some embodiments may be used to restore a multi-energy radiation image. For example, the X-ray detector 113 may be used to obtain a dual energy CT image or a dual energy X-ray image. Referring to FIG. 3A, an X-ray detector 113 according to certain embodiments includes a plurality of pixels 330 detecting radiation. Here, the pixel 330 may denote a unit detector detecting radiation, classifying photons according to energy bands, and counting the photons.

The X-ray detector 113 may include a sensor layer 310 and a PCD circuit layer 320. According to various embodiments, the sensor layer 310 may be provided on a front surface where X-rays are incident, and the PCD circuit layer 320 may be provided on a rear surface. Also, the sensor layer 310 and the PCD circuit layer 320 may be individual layers as shown in FIG. 3A.

The sensor layer 310 converts photons into an electric signal via a direct method. The sensor layer 310 may include, for example, cadmium telluride (CdTe). Alternatively, the sensor layer 310 may be formed of a semiconductor material other than CdTe. CdTe is a semiconductor material, and the PCD circuit layer 320 provided on the rear surface of the sensor layer 310 may also be formed of a semiconductor material. A bias voltage may be applied to the front surface of the sensor layer 310, and an electric signal is generated as charges generated by incident X-rays move through the sensor layer 310.

As used herein to describe certain embodiments, the 'front surface' and the 'rear surface' are relative terms, wherein a surface facing a radiation source emitting radiation to receive radiation is referred to as the front surface, and a surface that does not face the radiation source is referred to as the rear surface.

As shown in the non-limiting example of FIG. 3A, the plurality of pixels 330 may be arranged in a 2D array. Also, the plurality of pixels 330 may have tetrahedron structures having the same sizes. In the non-limiting example of FIG. 3A, 8*8=64 pixels are included in the X-ray detector 113.

In each of the plurality of pixels 330, sensor layer 310 may be provided on a front portion and the PCD circuit layer 320 may be provided on a rear portion. For example, the PCD circuit layer 320 may include a plurality of comparators and at least one counter so as to count photons of incident radiation and store the number of counted photons.

In detail, radiation passing through an object is incident on the front surface of the X-ray detector 113, and the sensor layer 310 provided on the front portion absorbs the incident radiation.

Also, the sensor layer 310 may be formed on at least a part of a surface facing the X-ray generator 112. In detail, the sensor layer 310 may be formed on at least a part of the front surface of the X-ray detector 113, which faces the X-ray generator 112, side surfaces of the surface facing the X-ray generator 112, or the rear surface of the X-ray detector 113, on which X-ray may be incident due to scattering of the X-ray generator 112. As shown in the non-limiting example of FIG. 3A, the sensor layer 310 is formed on the front surface of the X-ray detector 113, which faces the X-ray generator 112, in a uniform thickness.

According to some embodiments, a length of one side of the pixel 330 may be about 0.2 mm to 1.0 mm. For example, a front surface area of the pixel 330 may have a pixel size equal to or smaller than 1 mm$^2$.

Figure 3B:
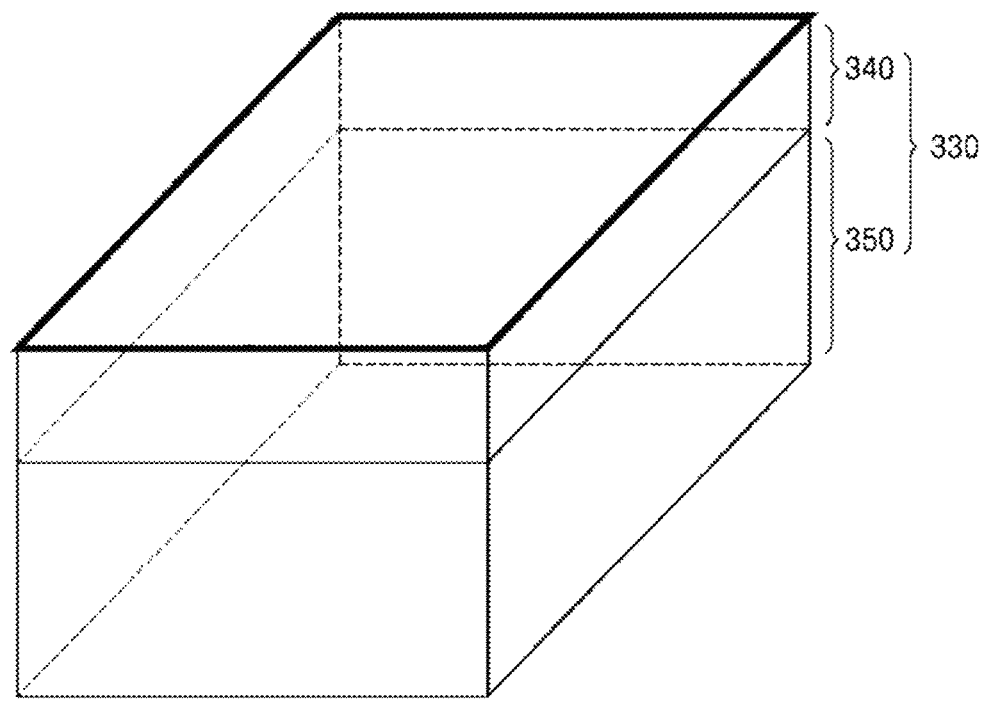
FIG. 3B illustrates a pixel, according to certain embodiments of this disclosure, such as embodiments shown in FIG. 3A.

FIG. 3B illustrates a pixel according to certain embodiments, such as pixel 330 of FIG. 3A. In detail, a sensor 340 provided on a front surface of the pixel 330 and a PCD circuit device 350 provided on a rear surface may respectively correspond to the sensor layer 310 and the PCD circuit layer 320 of FIG. 3A.

According to certain embodiments, sensor 340 generates a scan signal by converting photons to an electric signal, and outputs the scan signal to the PCD circuit device 350. The sensor 340 may be configured to be insulated from surrounding pixels 330. Also, the sensor 340 may include an electrode to output the scan signal to the PCD circuit device 350 through the electrode.

The X-ray detector 113 included in the CT system 100 absorbs a certain number of photons under a certain imaging condition. The number of photons absorbed and counted in one pixel having a unit area equal to or lower than 1 mm$^2$ may be determined according to spectrum modeling.

With respect to a PCD included in a high class type CT system, an imaging condition may be set such that a tube voltage is 120 kVp and a tube current is at least 200 mA, and a filter condition may be set such that an aluminum equivalent thickness is about 5.6 mm.

Under such an imaging condition, the number of photons to be absorbed and counted by one pixel may be calculated according to spectrum modeling of X-rays based on tungsten anode spectral model (TASMIP).

For example, the number of photons to be absorbed by one pixel per second may be about 2 hundred million to 5 hundred million. Here, one pixel may have a unit area equal to or lower than about 1 $mm^2$.

Figure 3C:
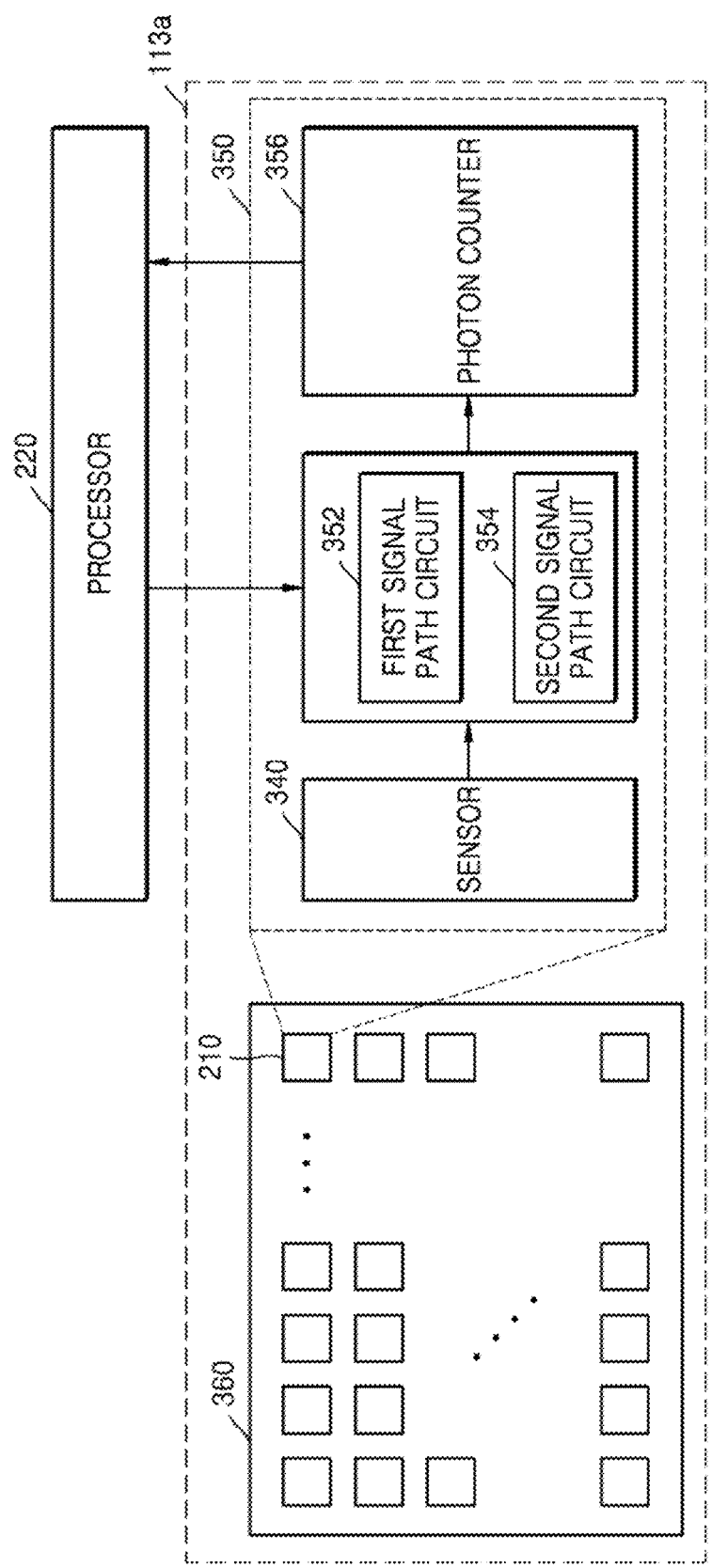
FIG. 3C illustrates a structure of a dual mode pixel together with a pixel array and a processor, according to various embodiments.

FIG. 3C illustrates a structure of a system comprising a dual mode pixel 210 comprising part of a pixel array and the processor 220, according to certain embodiments.

The X-ray detector 113 according to various embodiments may include a 2D pixel array 360. The 2D pixel array 360 may include at least one dual mode pixel 210.

According to some embodiments, some of the pixels 330 of the 2D pixel array 360 may be single mode PCD pixels, and the remaining may be the dual mode pixels 210. An arrangement of the single mode PCD pixels and the dual mode pixels 210 may vary according to embodiments. The processor 220 may output a mode selection signal with respect to dual mode pixels 210.

According to certain other embodiments, all pixels of the 2D pixel array 360 may be dual mode pixels 210.

As described above, in some embodiments, a dual mode pixel 210 may include the sensor 340 and the PCD circuit device 350. The PCD circuit device 350 may include a first signal path circuit 352, a second signal path circuit 354, and a photon counter 356.

As described above, the sensor 340 converts photos of radiation into a scan signal, i.e., an electric signal. The scan signal generated by the sensor 340 is transmitted to the photon counter 356 through the first or second signal path circuit 352 or 354. The first and second signal path circuits 352 and 354 are in a selective relationship, and the scan signal output from the sensor 340 is transmitted to the photon counter 356 through one of the first and second signal path circuits 352 and 354.

The processor 220 controls the scan signal to be transmitted through the first or second signal path circuit 352 or 354 by generating the mode selection signal and outputting the mode selection signal to the PCD circuit device 350 of the dual mode pixel 210. The processor 220 controls the scan signal to be transmitted through the first signal path circuit 352 in a first mode, and to be transmitted through the second signal path circuit 354 in a second mode. According to certain embodiments, the processor 220 may output the mode selection signal by determining an operation mode of each of the dual mode pixels 210. According to another embodiment, the dual mode pixels 210 may be divided into at least two groups, and the processor 220 may generate and output the mode selection signal with respect to each group of the dual mode pixels 210. The at least two groups of the dual mode pixels 210 may change according to an operation of the tomographic imaging apparatus 200a.

The first mode is an energy spectrum mode in which energy spectrum accuracy separation is high but a photo counting speed is lower than that of the second mode. The first mode may be used when energy spectrum resolution is required. In the first mode, the scan signal output from the sensor 340 is transmitted to the photon counter 356 through the first signal path circuit 352. The first signal path circuit 352 has high energy spectrum accuracy separation by including a pulse shaper. However, since the pulse shaper causes a delay in signal transmission, a dead time is generated due to the pulse shaper, and thus the photon counting speed is decreased. For the high energy spectrum accuracy separation, a long shaping time of the pulse shaper can be required, and thus the photon counting speed is decreased.

According to certain embodiments, the second mode is a mode having a high photon counting speed, and has a higher photon counting speed than that of the first mode. However, the second mode has lower energy spectrum accuracy separation than that of the first mode. The second mode may be used when photons need to be counted at a high speed. In the second mode, the scan signal output from the sensor 340 is transmitted to the photon counter 356 through the second signal path circuit 354. Since the second signal path circuit 354 does not include a pulse shaper, a dead time generated by a pulse shaper is removed, and thus photons may be counted at a high speed. Also, according to the second signal path circuit 354, the photons may be counted at a high speed by removing an output decay time of the pulse shaper in a Gaussian pulse shape. However, since the second signal path circuit 354 operates without a pulse shaper, energy spectrum accuracy separation may be lower than that of the first signal path circuit 352.

The photon counter 356 counts photons upon receiving the scan signal through the first or second signal path circuit 352 or 354. According to various embodiments, the photon counter 356 may include a counter corresponding to a plurality of energy levels to count photons by separating energy spectrum.

Figure 4:
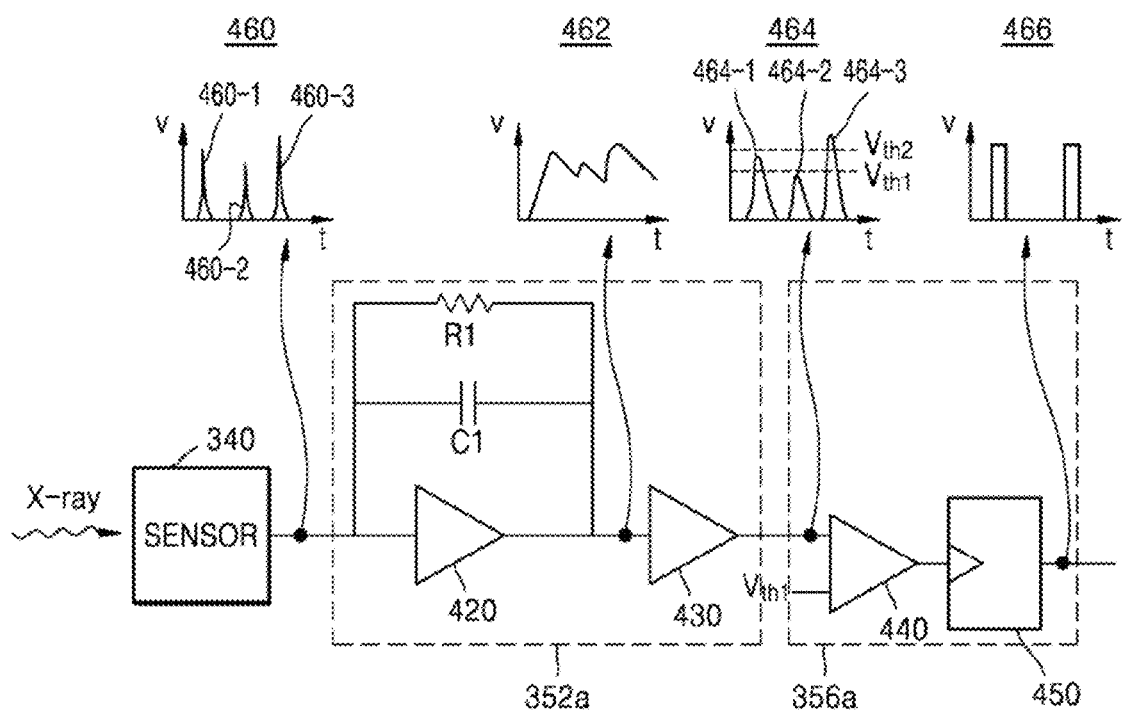
FIG. 4 illustrates a first signal path circuit according to some embodiments.

FIG. 4 illustrates a first signal path circuit 352a according to some embodiments.

The first signal path circuit 352a outputs an output signal 464 to a photon counter 356a by performing a pulse shaping process on an input signal 460. For example, as shown in FIG. 4, when the input signal 460 having three pulses 460-1 through 460-3 is input to the first signal path circuit 352a, the output signal 464 having three pulses 464-1 through 464-3, on which the pulse shaping process is performed.

The first signal path circuit 352a may include a first preamplifier 420, a first capacitor C1, a first resistor R1, and a pulse shaper 430. The first capacitor C1 and the first resistor R1 are connected in parallel between an input terminal and an output terminal of the first preamplifier 420. The input signal 460 output from the sensor 340 passes through the first preamplifier 420 and is amplified to a scan signal 462. The input signal 460 generated by charge packets generated by radiation incident on the sensor 340 is converted into a voltage signal by the first preamplifier 420. The scan signal 462 is input to the pulse shaper 430 and is again converted into the output signal 464 having the three pulses 464-1 through 464-3. In the output signal 464, intensity of each pulse is amplified compared to the input signal 460, while the pulses are more separated than in the scan signal 462, and thus it is possible to count photons by accurately separating the energy spectrum. In other words, via the pulse shaping process, the possibility of the photon counter 356a miscounting energy levels of photons may be decreased. However, during such a signal processing operation, a dead time is generated in the pulse shaper 430, and thus a photon counting speed may be lower than a second signal path circuit 354a.

Figure 5:
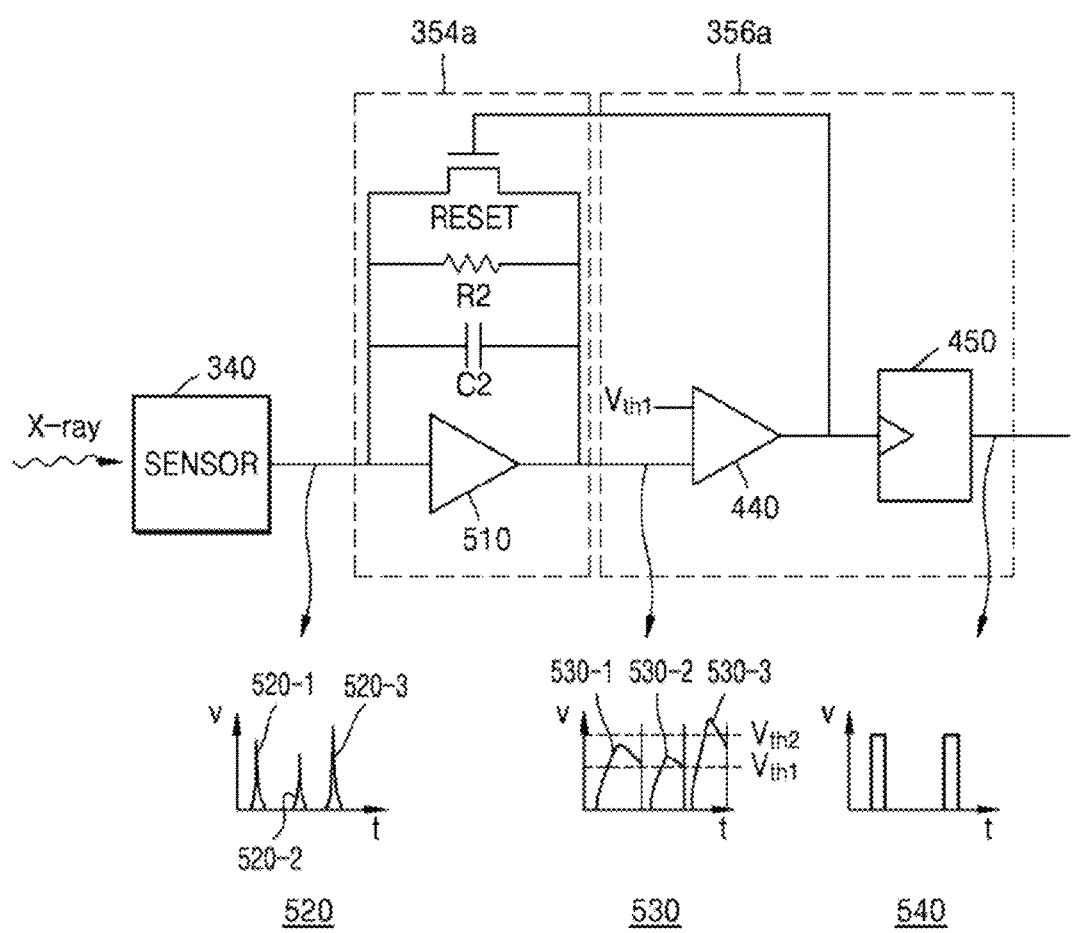
FIG. 5 illustrates a second signal path circuit according to certain embodiments.

FIG. 5 illustrates a second signal path circuit 354a according to certain embodiments.

Referring to the non-limiting example of FIG. 5, second signal path circuit 354a achieves a high photon counting speed by amplifying and resetting an input signal 520 at a high speed. For example, as shown in FIG. 5, when the input signal 520 having three pulses 520-1 through 520-3 is input to the second signal path circuit 354a, an amplification signal is output whenever the input signal 520 exceeds a certain first level.

The second signal path circuit 354a may include a second preamplifier 510, a second capacitor C2, a second resistor R2, and a reset switch RESET. The second capacitor C2, the second resistor R2, and the reset switch RESET are connected in parallel between an input terminal and an output terminal of the second preamplifier 510.

A control terminal of the reset switch RESET is connected to an output terminal of a comparator 440 of the photon counter 356a. According to another embodiment, the control terminal of the reset switch RESET is connected to an output terminal of the second preamplifier 510.

The input signal 520 output from the sensor 450 passes through the second preamplifier 510 and is amplified to a scan signal 530, i.e., a voltage signal. Here, when an output of the comparator 440 included in the photon counter 356a exceeds a certain level, the reset switch RESET is turned on, and levels at two ends of the second preamplifier 510 are reset. Since the second signal path circuit 354a does not include a pulse shaper, a period of time where the input signal 520 is input from the sensor 340 and output from the second signal path circuit 354a is shorter than that of the first signal path circuit 352a. Since the second signal path circuit 354a is reset and receives a scan signal again when the level of the scan signal 530 output from the second signal path circuit 354a exceeds at least one threshold voltage level, photons may be counted at a higher speed than when a pulse shaper outputting a Gaussian signal and having a long attenuation time is used. Accordingly, the second mode using the second signal path circuit 354a may have a higher photon counting speed than the first mode using the first signal path circuit 352a.

Radiation flux used in a tomographic imaging apparatus for medical diagnosis is about $10^8$ to $10^9$ photons/sec*$mm^2$. A photon counting speed is important in counting photons at a certain location for a short period of time while the X-ray generator 112 of the tomographic imaging apparatus rotates at a high speed, and energy spectrum accuracy is important in distinguishing intensities of photons incident on a detector. However, it is difficult to achieve a high photon counting speed and energy spectrum accuracy at the same time due to contradiction in a pulse shaper. An energy level of a pulse signal is accurately determined as the pulse signal output from a preamplifier passes through a pulse shaper, but a photon counting speed may be decreased as a dead time, in which a signal input while a pulse is being shaped is lost without being processed, occurs. When the pulse shaper is removed and only a signal equal to or higher than a threshold value is received and reset so as to increase the photon counting speed, a dead time may be reduced but only a signal of a limited energy size may be detected, and two or more signals may overlap for several nano-seconds due to a pulse pile-up phenomenon, and thus the signals may be determined to be larger than they actually are.

According to one or more embodiments, a detector using a photon counting method may select, with respect to one pixel, a first mode corresponding to an energy spectrum method having excellent energy resolution or a second mode corresponding to a high counting method having ha high photon counting speed. Consequently, according to one or more embodiments, one pixel may selectively use one of two modes. A dual mode pixel may include as many circuits as possible within a limited area according to development of semiconductor integrated circuit techniques, and thus may be embodied in a limited area and have high performance.

Figure 6:
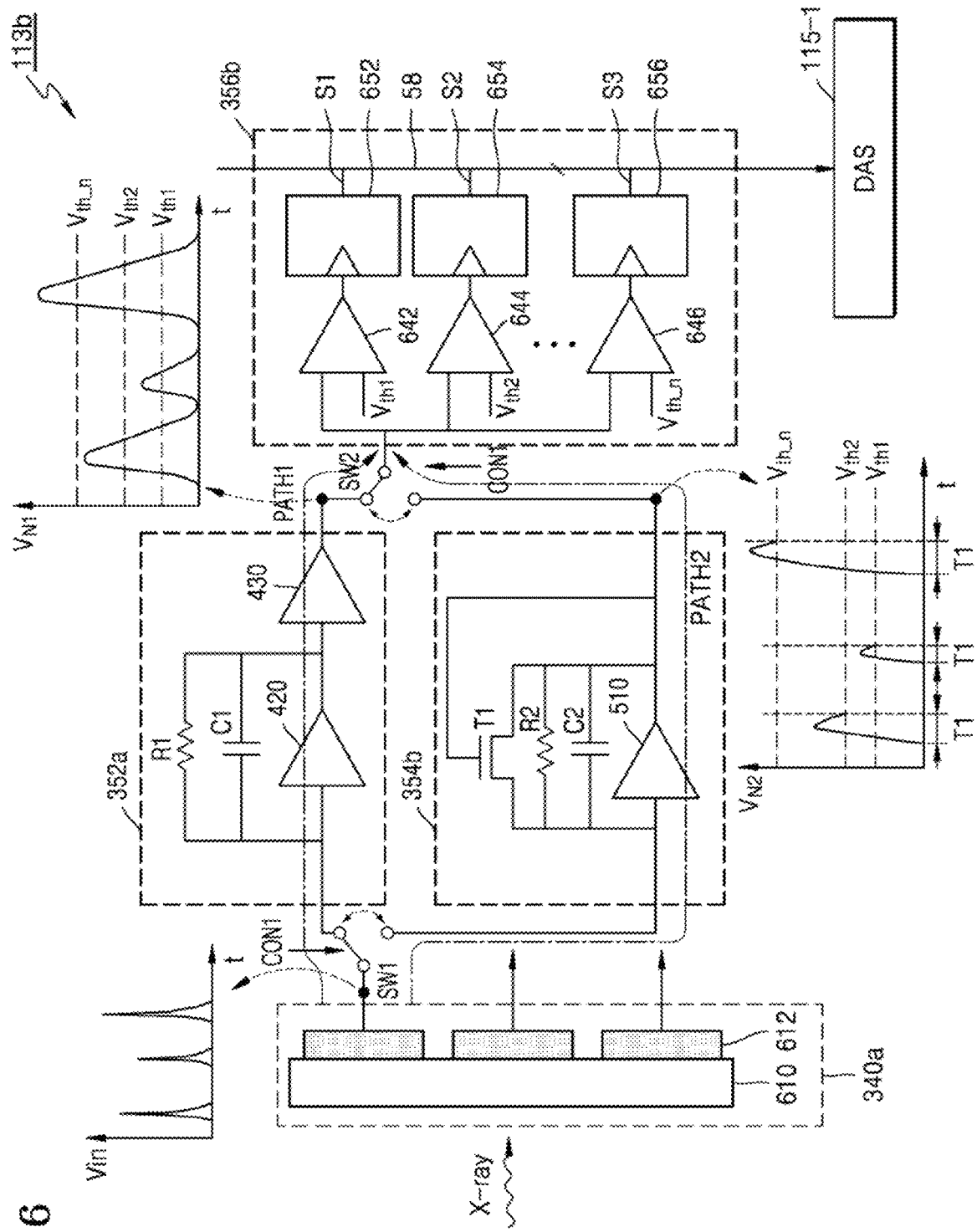
FIG. 6 illustrates an X-ray detector according to various embodiments.

FIG. 6 illustrates an X-ray detector 113b according to various embodiments.

Referring to the non-limiting example of FIG. 6 X-ray detector 113b according to the current embodiment includes a sensor 340a, a first switch SW1, the first signal path circuit 352a, a second signal path circuit 354b, a second switch SW2, and a photon counter 356b.

According to the some embodiments, a scan signal may be transmitted through a first path PATH1 connecting the sensor 340a, the first signal path circuit 352a, and the photon counter 356b in a first mode, and through a second path PATH2 connecting the sensor 340a, the second signal path circuit 354b, and the photon counter 356b in a second mode.

In the non-limiting example of FIG. 6, transmission path of the scan signal is determined by a mode selection signal CON1 output from the processor 220. According to various embodiments, the processor 220 may generate and output the mode selection signal CON1 with respect to each dual mode pixel 210. According to another embodiment, the dual mode pixels 210 may be grouped into a certain number of groups, and the processor 220 may generate and output the mode selection signal CON1 with respect to each groups of the dual mode pixels 210. The groups of the dual mode pixels 210 may be determined during a product design stage, determined automatically based on an operation mode of the tomographic imaging apparatus 200a, or determined based on a user input.

The mode selection signal CON1 is input to the first and second switches SW1 and SW2 of each dual mode pixel 210.

The first switch SW1 may include one input terminal, two output terminals, and a control terminal. The first switch SW1 may output a signal input to the input terminal to one of the two output terminals based on the mode selection signal CON1 input through the control terminal. According to certain embodiments, the input terminal of the first switch SW1 is connected to an electrode 612 of the sensor 340a, and the two output terminals of the first switch SW1 may be respectively connected to the input terminal of the first signal path circuit 352a and the input terminal of the second signal path circuit 354b.

The second switch SW2 may include two input terminals, one output terminal, and a control terminal. The two input terminals of the second switch SW2 may be respectively connected to the output terminal of the first signal path circuit 352a and the output terminal of the second signal path circuit 354b, and the output terminal of the second switch SW2 may be connected to an input terminal of the photon counter 356b.

The first and second switches SW1 and SW2 are individually provided with respect to each dual mode pixel 210. When the X-ray detector 113b includes a plurality of pixels and some of the plurality of pixels are embodied as the dual mode pixels 210, the first and second switches SW1 and SW2 may not be provided for normal pixels, but may be provided only for the dual mode pixels 210.

The first and second switches SW1 and SW2 switch a signal transmission path according to the mode selection signal CON1.

When the first mode is selected by the mode selection signal CON1, the first switch SW1 generates a signal transmission path between the sensor 340a and the first signal path circuit 352a, and blocks a signal transmission path between the sensor 340a and the second signal path circuit 354b. Also, when the first mode is selected by the mode selection signal CON1, the second switch SW2 generates a signal transmission path between the first signal path circuit 352a and the photon counter 356b, and blocks a signal transmission path between the second signal path circuit 354b and the photon counter 356b. Accordingly, when the first mode is selected by the mode selection signal CON1, the scan signal is transmitted through the first path PATH1 connecting the sensor 340a, the first signal path circuit 352a, and the photon counter 356b.

When the second mode is selected by the mode selection signal CON1, the first switch SW1 generates a signal transmission path between the sensor 340a and the second signal path circuit 354b, and blocks a signal transmission path between the sensor 340a and the first signal path circuit 352a. Also, when the second mode is selected by the mode selection signal CON1, the second switch SW2 generates a signal transmission path between the second signal path circuit 354b and the photon counter 356b, and blocks a signal transmission path between the first signal path circuit 352a and the photon counter 356b. Accordingly, when the second mode is selected by the mode selection signal CON1, the scan signal is transmitted through the second path PATH2 connecting the sensor 340a, the second signal path circuit 354b, and the photon counter 356b.

According to various embodiments, the sensor 340a includes a photoelectric conversion layer 610 and an electrode 612.

According to various embodiments, the photoelectric conversion layer 610 may include a CdTe layer. According to another embodiment, the photoelectric conversion layer 610 may include a scintillator converting X-rays to visible rays, and a photodiode converting the visible rays to an electric signal. The photoelectric conversion layer 610 may be configured to be insulated in pixel units or sub-pixel units. The photoelectric conversion layer 610 may convert photons into a hole-electron pair to generate an electric signal corresponding to energy of the photons. Also, the electric signal may be a voltage signal or a current signal. In the current specification, the electric signal is a voltage signal.

The electrode 612 may be provided on a rear surface of the photoelectric conversion layer 610 in a pattern corresponding to each pixel or sub-pixel. The rear surface of the photoelectric conversion layer 610 denotes a rear surface with respect to an X-ray incident surface. The electrode 612 may include a metal having high conductivity. A scan signal generated by the photoelectric conversion layer 610 is transmitted to the input terminal of the first switch SW1.

In the first mode, the scan signal output from the sensor 340a is input to the first signal path circuit 352a through the first switch SW1. Then, the scan signal is amplified in the first signal path circuit 352a, and is input to the photon counter 356a through the second switch SW2 via a pulse shaping process. The first signal path circuit 352a of FIG. 6 has, in certain embodiments, the same structure as the first signal path circuit 352a of FIG. 4, and thus details thereof are not provided again.

In the second mode, the scan signal output from the sensor 340a is input to the second signal path circuit 354b through the first switch SW1. Then, the scan signal is amplified in the second signal path circuit 354b, and is input to the photon counter 356a through the second switch SW2. The second signal path circuit 354b of FIG. 6 includes the second preamplifier 510, the second capacitor C2, the second resistor R2, and the reset switch RESET. The second capacitor C2, the second resistor R2, and the reset switch RESET is connected in parallel between the input terminal and the output terminal of the second preamplifier 510. The control terminal of the reset switch RESET is connected to the output terminal of the second preamplifier 510. According to the current embodiment, the reset switch RESET is turned on when a first reference time T1 is passed after a pulse of the scan signal output from the sensor 340a is input to the second preamplifier 510. Accordingly, levels of the input and output terminals of the second preamplifier 510 of the second signal path circuit 354b are reset whenever the first reference time T1 is passed after the pulse of the scan signal output from the sensor 340a is input to the second preamplifier 510.

The photon counter 356b receives the scan signal from the first or second signal path circuit 352a or 354b through the second switch SW2. According to certain embodiments, the photon counter 356b may include first through third comparators 642 through 646 respectively corresponding to different first through nth threshold voltages Vth1 through Vth_n, and first through third counters 652 through 656.

The first through third comparators 642 through 646 each receive a scan signal and a reference voltage. The first through nth threshold voltages Vth1 through Vth_n of the first through third comparators 642 through 646 may be set according to energy levels that are distinguished and counted. When a pulse of a scan signal exceeding the first through nth threshold voltages Vth1 through Vth_n of the first through third comparators 642 through 646 is received, the first through third comparators 642 through 646 may generate an output signal of a high level and output the output signal respectively to the first through third counters 652 through 656 connected to the first through third comparators 642 through 646. When the output signal of the high level is received from the first through third comparators 642 through 646, the first through third counters 652 through 656 may output the output signal of the high level to the DAS 115-1.

An output line 658 connected to the first through third counters 652 through 656 may be individually embodied with respect to the first through third counters 652 through 656 or may be embodied in one line.

Figure 7:
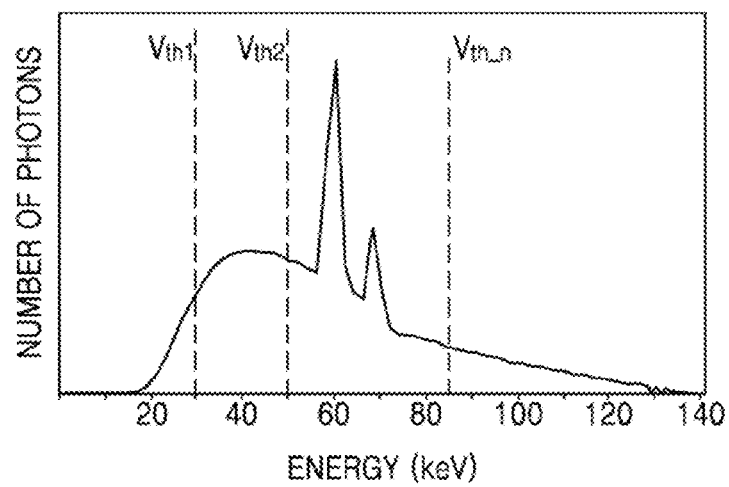
FIG. 7 illustrates energy distribution of photons incident on an X-ray detector observed in certain embodiments according to this disclosure.

FIG. 7 illustrates an energy distribution of photons incident on an X-ray detector according to certain embodiments.

Referring to the non-limiting example of FIG. 7, an x-axis indicates an energy size of photons, and a y-axis indicates the number of photons incident on a front surface of the X-ray detector 113 in a certain area. Also, the graph of FIG. 7 indicates an energy spectrum of photons incident on the X-ray detector 113.

The X-ray generator 112 may generate and emit X-rays upon receiving a voltage or a current through a high voltage generator (not shown). The X-rays generated and emitted from the X-ray generator 112 may have an energy spectrum as shown in the non-limiting example of FIG. 7. Also, photons of radiation emitted from the X-ray generator 112 and passed through an object the X-ray generator 112 may have an energy spectrum modified from that of FIG. 7. The tomographic imaging apparatus 200a may obtain information about the modified energy spectrum to generate a tomographic image of the object.

The X-ray detector 113 according to various embodiments may classify and count the photons according to the energy size of the photons. The first through nth threshold voltages Vth1 through Vth_n used to classify the energy size of the photons may be determined as shown in FIG. 7 based on an energy spectrum of X-rays output from an X-ray tube (not shown) of the X-ray generator 112. For example, the first threshold voltage Vth1 may have a level corresponding to 30 eV, the second threshold voltage Vth2 may have a level corresponding to 50 eV, and the nth threshold voltage Vth_n may have a level corresponding to 85 eV. The numbers of comparators and counters included in the photon counter 356b may be variously determined according to embodiments. Also, the levels of the first through nth threshold voltages Vth1 through through Vth_n of the first through third comparators 642 through 646 may be variously determined according to embodiments.

According to various embodiments, the levels of first through nth threshold voltages Vth1 through through Vth_n may vary according to a user input or an operation mode of the tomographic imaging apparatus 200a. For example, the levels of first through nth threshold voltages Vth1 through through Vth_n may be determined based on an energy level desired by a user.

Figure 8A:
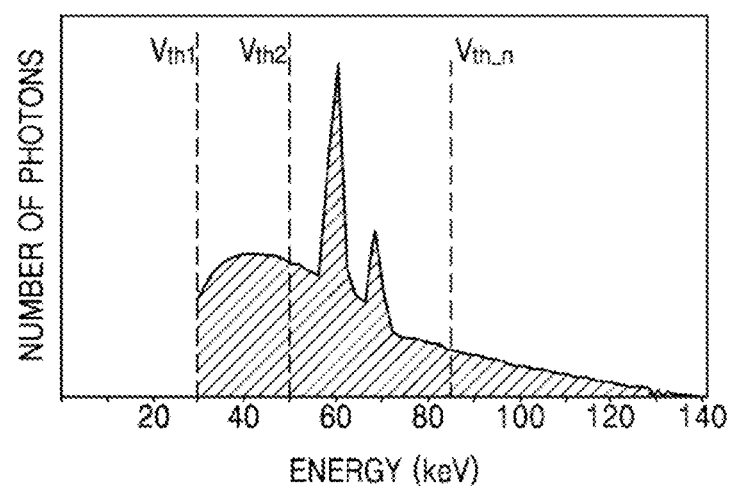
FIGS. 8A through 8C illustrates aspects of the operation operations of tomographic imaging apparatus according to some embodiments.
Figure 8B:
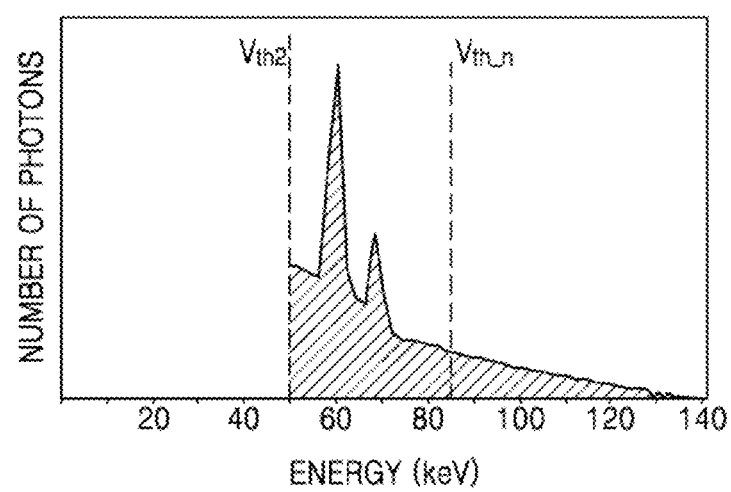
Figure 8C:
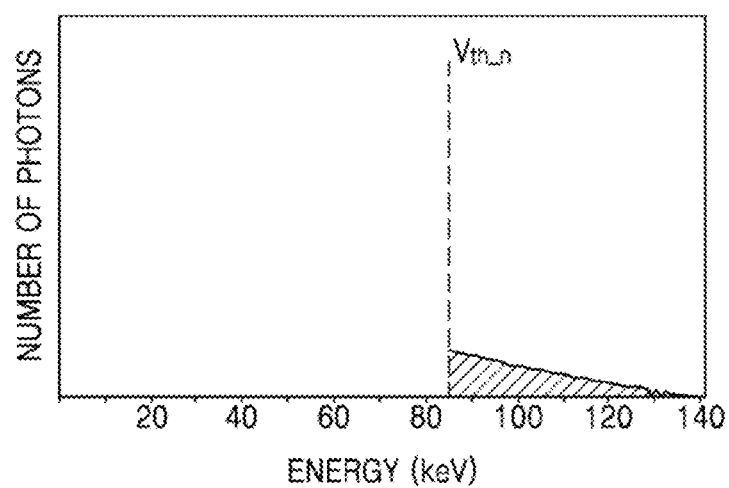

FIGS. 8A through 8C illustrate aspects of operations of tomographic imaging apparatus 100a according to various embodiments. In the non-limiting examples of FIGS. 8A through 8C, an x-axis indicates an energy size of photons, and a y-axis indicates the number of photons incident on a front surface of the X-ray detector 113 in a certain area.

FIG. 8A illustrates an energy range of photons counted by a first comparator 642 and a first counter 652 according to certain embodiments. The first comparator 642 and the first counter 652 count the number of photons having an energy level higher than the first threshold voltage Vth1, and output first scan data S1. A tomographic image restored based on the first scan data S1 may indicate information about regions having an energy level higher than the first threshold voltage Vth1.

FIG. 8B illustrates an energy range of photons counted by the second comparator 644 and the second counter 654. The second comparator 644 and the second counter 654 count the number of photons having an energy level higher than the second threshold voltage Vth2, and output second scan data S2. A tomographic image restored based on the second scan data S1 may indicate information about regions having an energy level higher than the second threshold voltage Vth2.

FIG. 8C illustrates an energy range of photons counted by the third comparator 646 and the third counter 656. The third comparator 646 and the third counter 656 count the number of photons having an energy level higher than the third threshold voltage Vth3, and output third scan data S3. A tomographic image restored based on the third scan data S3 may indicate information about regions having an energy level higher than the third threshold voltage Vth3.

According to certain embodiments, the processor 220 may calculate the number of photons having an energy level between the first and second threshold voltages Vth1 and Vth2 and the number of photons having an energy level between the second and third threshold voltages Vth2 and Vth3 by using the first through third scan data S1 through S3. For example, the processor 220 may calculate the number of photons having the energy level between the first and second threshold voltages Vth1 and Vth2 by calculating a difference between the first and second scan data S1 and S2. Also, the processor 220 may calculate the number of photons having the energy level between the second and third threshold voltages Vth2 and Vth3 by calculating a difference between the second and third scan data S2 and S3.

According to various embodiments, when the dual mode pixel 210 operates in the first mode, the processor 220 may increase the number of threshold voltages and decrease a difference between energy levels of the threshold voltages compared to the second mode. Also, when the dual mode pixel 210 operates in the second mode, the processor 220 may decrease the number of threshold voltages and increase a difference between energy levels of the threshold voltages compared to the first mode. In the first mode, since an energy level of each pulse of a scan signal is accurately measured via a pulse shaping operation, the number of threshold voltages may be increased to obtain an energy spectrum having enhanced energy resolution. In the second mode, as a transmission speed of a scan signal is increased, energy resolution may be somewhat sacrificed and intensity of the scan signal of each energy level may be accurately measured.

According to various embodiments, since each dual mode pixel 210 operates in one of the first mode, in which resolution of an energy spectrum is enhanced, and the second mode, in which a photon counting speed is increased, based on a pixel location or an operation mode of the tomographic imaging apparatus 200a, photons may be effectively counted with respect to each energy level. For example, when the tomographic imaging apparatus 200a operates in a high speed rotation mode, the processor 220 may control the dual mode pixels 210 to operate in the second mode so as to accurately measure intensity of a signal in each energy level. As another example, when the tomographic imaging apparatus 200a performs imaging using a contrast medium, the processor 220 may control the dual mode pixels 210 to operate in the first mode so as to enhance resolution of an energy level. As another example, when the tomographic imaging apparatus 200a performs tomography with respect to a moving object (for example, a heart or a blood vessel), the processor 220 may control the dual mode pixels 210 to operate in the second mode to increase a photon counting speed.

Figure 9:
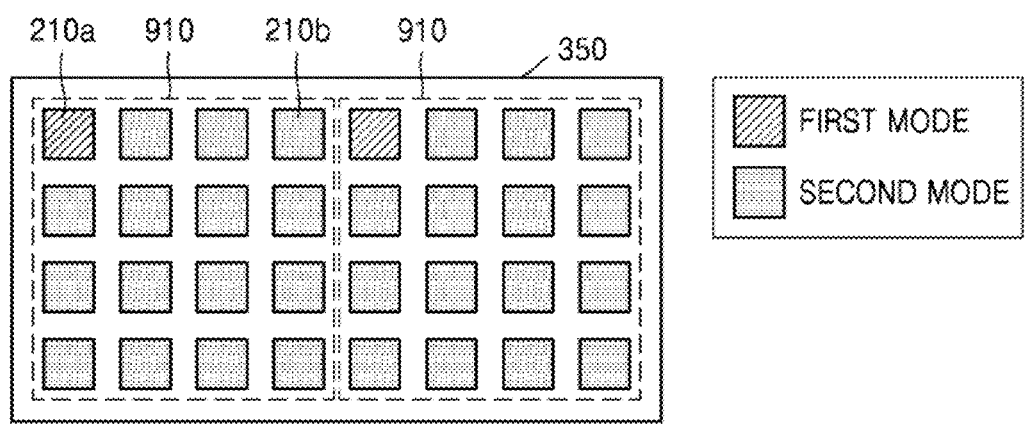
FIG. 9 illustrates operation modes of dual mode pixels according to certain embodiments.

FIG. 9 illustrates aspects of operation modes of dual mode pixels 210a and 210b according to certain embodiments.

According to various embodiments, each of the dual mode pixels 210a and 210b is a binning sub-pixel, and the certain number of dual mode pixels 210a and 210b may form one binning pixel. For example, 16 dual mode pixels 210a and 210b arranged in 4×4 may correspond to one binning pixel. The arrangement and number dual mode pixels 210a and 210b forming one binning pixel may vary according to embodiments. For example, the number of binning sub-pixels included in one binning pixel may be 4*6=24, 5*5=25, or 6*6=36.

According to various embodiments, some of a plurality of dual mode pixels included in a binning pixel 910 may operate in the first mode and the remaining may operate in the second mode. For example, as shown in FIG. 9, 16 (4×4) dual mode pixels 210a and 210b may be included in the binning pixel 910, wherein one dual mode pixel 210a may operate in the first mode and the remaining 15 dual mode pixels 210b may operate in the second mode. The processor 220 may output a mode selection signal for selecting the first mode to the dual mode pixel 210a that is to operate in the first mode, and a mode selection signal for selecting the second mode to the dual mode pixels 210b that are to operate in the second mode. Accordingly, an energy spectrum of the binning pixel 910 may be accurately calculated by the dual mode pixel 210a operating in the first mode, and the number of photons incident on the binning pixel 910 may be accurately counted by the dual mode pixels 210b operating in the second mode. The processor 220 may replace the energy spectrum of the binning pixel 910 by the energy spectrum of the dual mode pixel 210a in the first mode.

The number and arrangement of the dual mode pixels 210a to be operated in the first mode in the binning pixel 910 may vary according to embodiments.

Figure 10:
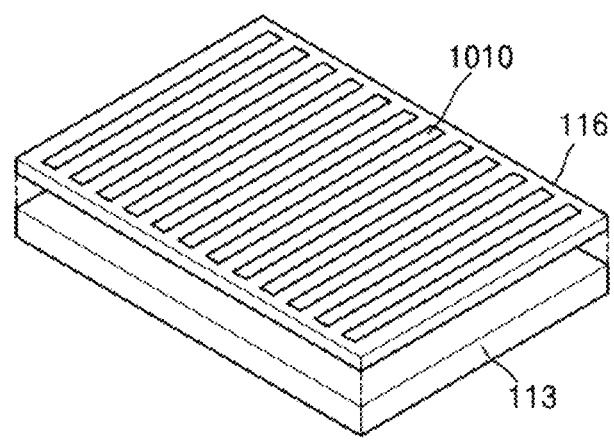
FIG. 10 illustrates an anti-scatter grid and an X-ray detector, according to various embodiments.

FIG. 10 illustrates an anti-scatter grid 116 and an X-ray detector 113, according to certain embodiments.

According to various embodiments, the anti-scatter grid 116 may be provided on the front surface of the X-ray detector 113 on which X-rays are incident. The anti-scatter grid 116 is provided between the object and the X-ray detector 113, and may transmit most of primary radiation and attenuate scatter radiation. In other words, the anti-scatter grid 116 is disposed on the X-ray detector 113 to block non-linear photons and prevent scattering of X-rays. The anti-scatter grid 116 may be embodied by using, for example, tungsten.

The anti-scatter grid 116 may have any one of various forms, for example, a form in which an opening 1010 formed by a frame extending in one direction is repeated as shown in FIG. 10, or a form in which an opening formed by a frame having a lattice shape is repeated. When the anti-scatter grid 116 is provided on the X-ray detector 113, the X-ray detector 113 may have a region covered by the anti-scatter grid 116, and a distortion phenomenon may be generated due to scattering of energy.

Figure 11:
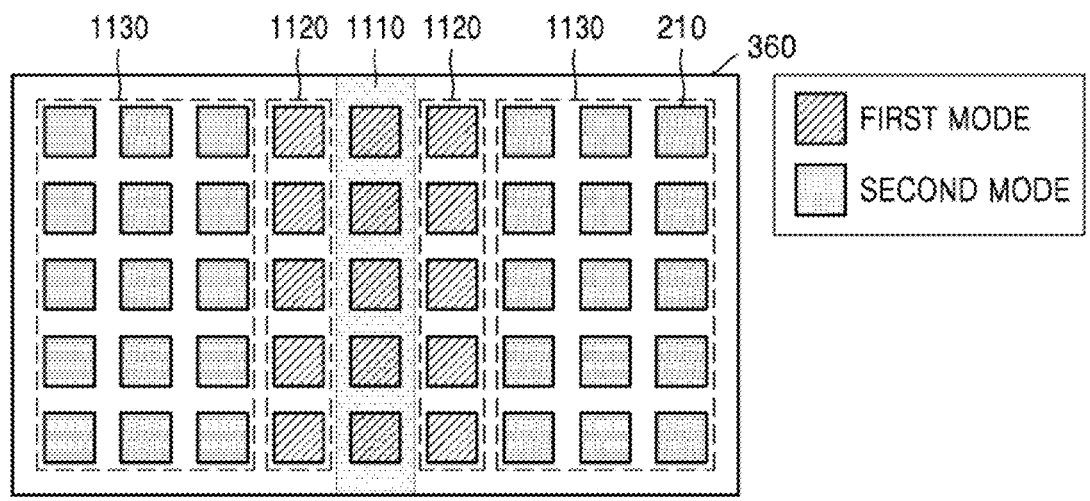
FIG. 11 illustrates a pixel array according to some embodiments.

FIG. 11 illustrates a 2D pixel array 360 according to various embodiments.

According to certain embodiments, dual mode pixels 1120 around a region 1110 covered by the anti-scatter grid 116 may be operated in the first mode and the remaining pixels 1130 may be operated in the second mode. The processor 220 may output a mode selection signal for selecting the first mode to the dual mode pixels 1120 around the region 1110 covered by the anti-scatter grid 116, and output a mode selection signal for selecting the second mode to the remaining pixels 1130.

According to the some embodiments, a distortion phenomenon generated in the region 1110 covered by the anti-scatter grid 116 due to scattering of energy may be compensated for. Since the number of photons incident on the dual mode pixels 1120 around the region 1110 covered by the anti-scatter grid 116 is highly likely to be lower than that on the remaining pixels 1130, the importance of detecting an accurate energy spectrum is higher than the necessity of a high photon counting speed. Accordingly, in the some embodiments, the dual mode pixels 1120 in a region having low necessity of a high photon counting speed are operated in the first mode to enhance resolution of an energy spectrum, and thus the dual mode pixels 1120 may be effectively used.

Figure 12:
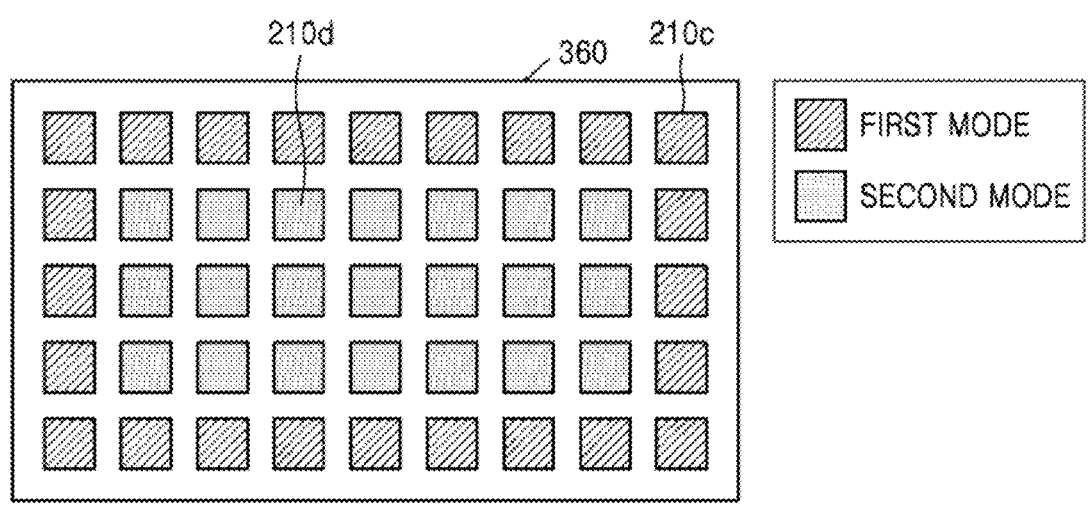
FIG. 12 illustrates a pixel array according to some embodiments.

FIG. 12 illustrates a 2D pixel array 360 according to various embodiment.

Referring to the non-limiting example of FIG. 12, dual mode pixels 210*c* in a peripheral region of the 2D pixel array 360 may be operated in the first mode, and the remaining dual mode pixels 210*d* of the 2D pixel array 360 may be operated in the second mode. The processor 220 may output a mode selection signal for selecting the first mode to the dual mode pixels 210 in the peripheral region and output a mode selection signal for selecting the second mode to the remaining dual mode pixels 210*d*.

Here, the peripheral region denotes a region corresponding to an outer region of the 2D pixel array 360. A region corresponding to the peripheral region may be expanded or reduced according to embodiments. The number of dual mode pixels 210*c* included in the peripheral region may vary according to embodiments.

Pixels in a peripheral region may have a relatively high noise level due to a leakage current or the like and are highly likely to be distorted, and thus the processor 220 may perform a post-process operation, such as calibration, so as to compensate for noise and distortion. According to the current embodiment, by operating the dual mode pixels 210*c* in the peripheral region in the first mode, an accurate energy spectrum is obtained from the dual mode pixels 210*c*, and thus the processor 220 may accurately perform a compensation operation on distortion. Also, according to the current embodiment, by enhancing functions of a distortion compensation operation, a tomographic image having higher quality may be obtained.

Figure 13:
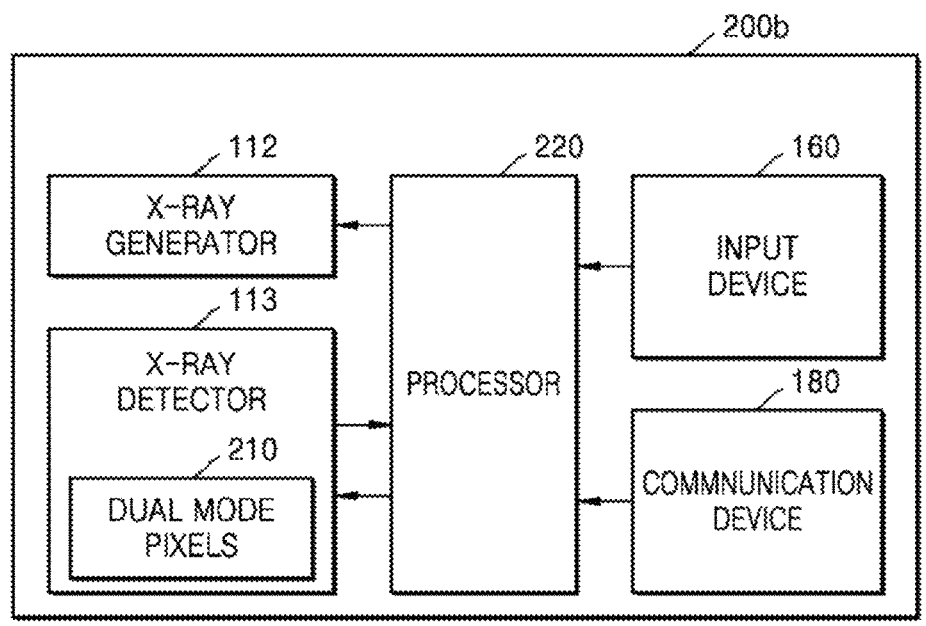
FIG. 13 illustrates, in block diagram format, a tomographic imaging apparatus according to certain embodiments.

FIG. 13 illustrates, in block diagram format a structure of a tomographic imaging apparatus 200*b* according to various embodiments.

The tomographic imaging apparatus 200*b* according to certain embodiments includes the X-ray generator 112, the X-ray detector 113, the processor 220, an input device 160, and a communication interface 180. According to various embodiments, the tomographic imaging apparatus 200*b* may include one of the input device 160 and the communication interface 180. The X-ray detector 113 includes the plurality of dual mode pixels 210. Details of FIG. 13, which overlap those of FIG. 2, are not provided again here.

Referring to the non-limiting example of FIG. 13, X-ray generator 112 generates and emits X-rays by receiving a voltage or a current from a HVG. According to various embodiments, a mode of the dual mode pixel 210 may be determined according to a tube voltage and a tube current of the X-ray generator 112. For example, the processor 220 may increase a ratio of the dual mode pixels 210 operating in the second mode when an energy level (eV value) determined by the tube voltage and the tube current of the X-ray generator 112 increases.

Also, the processor 220 may adjust levels of the first through nth threshold voltages Vth1 through Vth_n used in a photon counter of the dual mode pixel 210 based on the tube voltage and the tube current of the X-ray generator 112. For example, when the photon counter uses the first through third threshold voltages Vth1 through Vth3, the processor 220 may set the first through third threshold voltages Vth1 through Vth3 based on levels of the tube voltage and the tube current of the X-ray generator 112 such that a first photon counter (the first comparator 642 and the first counter 652 of FIG. 6) counts photons having energy equal to or higher than 30 keV, a second photon counter (the second comparator 644 and the second counter 654 of FIG. 6) counts photons having energy equal to or higher than 60 keV, and a third photon counter (the third comparator 646 and the third counter 656 of FIG. 6) counts photons having energy equal to or higher than 90 keV.

Also, according to certain embodiments, the processor 220 may determine an operation mode of the plurality of dual mode pixels 210 based on a first control signal received through the input device 160. The input device 160 receives a control signal, data, or the like from the user. The input device 160 may include, for example, a key, a jog, a knob, a touch panel, a touch screen, a keyboard, a while, a mouse, or the like. Also, the tomographic imaging apparatus 200*b* may provide a UI view through a display so as to provide a UI enabling the user to select a mode of the dual mode pixel 210. The processor 220 may determine operation modes of the plurality of dual mode pixels 210 based on a user input received through the input device 160.

According to various embodiments, a user input may be an input of selecting one of a plurality of pre-set options. For example, the tomographic imaging apparatus 200*b* may provide, through a UI view, a first option in which one dual mode pixel from among sub-pixels in a binning pixel is operated in the first mode and the remaining dual mode pixels are operated in the second mode, a second option in which dual mode pixels in a peripheral region are operated in the first mode and the remaining dual mode pixels are operated in the second mode, and a third option in which dual mode pixels in a region assigned by the user are operated in the first mode and dual mode pixels in the remaining region are operated in the second mode, and the user may select one of the first through third options.

According to another embodiment, the user input may be an input of directly assigning a dual mode pixel to be operated in the first mode and a dual mode pixel to be operated in the second mode. For example, the display may provide a UI view indicating all dual mode pixels, and the user may directly assign the dual mode pixel to be operated in the first mode and the dual mode pixel to be operated in the second mode from among the all dual mode pixels.

According to various embodiments, such a user input for determining an operation mode of a dual mode pixel may be input through the communication interface 180. The communication interface 180 may include at least one component enabling communication with an external apparatus, and for example, may include at least one of a near field communication module, a wired communication module, and a wireless communication module. According to certain embodiments, as described above, the signal of selecting one of the plurality of options or the control signal of directly assigning a mode of a dual mode pixel may be input to the processor 220 through the communication interface 180. According to the current embodiment, the user may control the tomographic imaging apparatus 200b remotely by using a communication terminal, a tablet PC, a smart phone, or a workstation.

The processor 220 may generate and output a mode selection signal by determining the operation modes of the plurality of dual mode pixels 210 based on the control signal input through the input device 160 or the communication interface 180.

According to various embodiments, the processor 220 may adjust the numbers or ratio of dual mode pixels operating in the first mode and the dual mode pixels operating in the second mode, according to a type of protocol performed by the tomographic imaging apparatus 200b. Also, the processor 220 may adjust locations of the dual mode pixels operating in the first mode and the dual mode pixels operating in the second mode, according to a type of protocol performed by the tomographic imaging apparatus 200b. For example, the processor 220 may control the all dual mode pixels 210 to operate in the first mode or set a ratio of the dual mode pixels 210 operating in the first mode to be high during multi-energy imaging using a contrast medium. As another example, the processor 220 may control the all dual mode pixels 210 to operate in the second mode or set a ratio of the dual mode pixels 210 operating in the second mode to be high when an image of a moving object (for example, a heart or a blood vessel) is captured. As another example, the processor 220 may control the all dual mode pixels 210 to operate in the second mode or set the ratio of the dual mode pixels 210 operating in the second mode to be high when high speed rotation photographing is performed.

Figure 14:
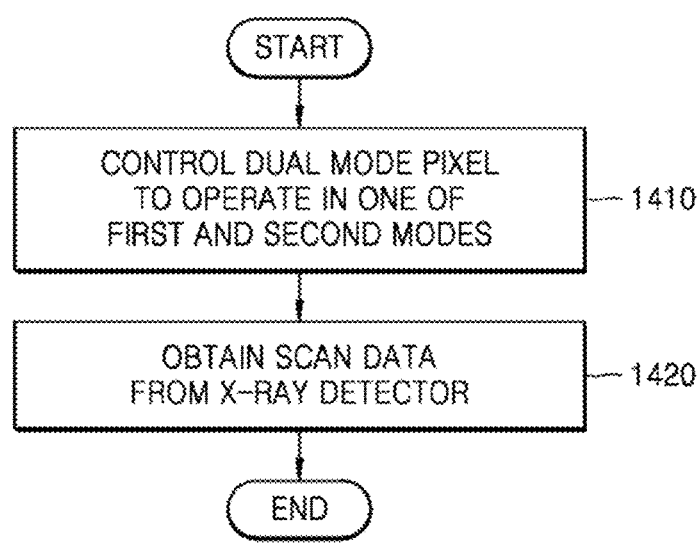
FIG. 14 illustrates operations of a method of controlling a tomographic imaging apparatus, according to various embodiments.

FIG. 14 illustrates operations of a method of controlling a tomographic imaging apparatus, according to various embodiments.

Referring to the non-limiting example of FIG. 14, methods according to certain embodiments may be performed by a tomographic imaging apparatus including a dual mode pixel. As described above, the dual mode pixel is a pixel included in an X-ray detector, such as a PCD, and is a pixel including first and second signal path circuits selectively transmitting a scan signal. In certain embodiments, the method is performed by the tomographic imaging apparatus 200a or 200b of FIG. 2 or 13, but the scope of the present disclosure is not limited thereto. Embodiments of the tomographic imaging apparatuses 200a and 200b described above may also be applied to the method.

According to various embodiments, the processor 220 controls a dual mode pixel of the X-ray detector 113 to operate in one of the first and second modes, in operation 1410. The processor 220 generates a mode selection signal with respect to the dual mode pixels by determining operation modes of the dual mode pixels, and output the mode selection signal to each dual mode pixel. As described above, selecting of the operation modes of the dual mode pixels may vary according to embodiments.

Then, the processor 220 obtains scan data from the X-ray detector 113 in operation 1420.

The embodiments may be implemented as a software program including instructions stored in a computer-readable storage medium.

A computer may refer to a device configured to retrieve an instruction stored in the computer-readable storage medium and to operate, in response to the retrieved instruction, and may include an tomographic imaging apparatus according to embodiments.

The computer-readable storage medium may be provided in the form of a non-transitory storage medium. In this regard, the term 'non-transitory' means that the storage medium does not include a signal and is tangible, and the term does not distinguish between data that is semi-permanently stored and data that is temporarily stored in the storage medium.

In addition, the tomographic imaging apparatus or the method of controlling the tomographic imaging apparatus according to embodiments may be provided in the form of a computer program product. The computer program product may be traded, as a product, between a seller and a buyer.

The computer program product may include a software program and a computer-readable storage medium having stored thereon the software program. For example, the computer program product may include a product (e.g. a downloadable application) in the form of a software program electronically distributed by a manufacturer of the tomographic imaging apparatus or through an electronic market (e.g., GOOGLE™, PLAY STORE™, and APP STORE™). For such electronic distribution, at least a part of the software program may be stored on the storage medium or may be temporarily generated. In this case, the storage medium may be a storage medium of a server of the manufacturer, a server of the electronic market, or a relay server for temporarily storing the software program.

In a system consisting of a server and a terminal (e.g., the tomographic imaging apparatus), the computer program product may include a storage medium of the server or a storage medium of the terminal. Alternatively, in a case where a third device (e.g., a smartphone) that communicates with the server or the terminal is present, the computer program product may include a storage medium of the third device. Alternatively, the computer program product may include a software program that is transmitted from the server to the terminal or the third device or that is transmitted from the third device to the terminal.

In certain embodiments according to this disclosure, one of the server, the terminal, and the third device may execute the computer program product, thereby performing the method according to embodiments. Alternatively, at least two of the server, the terminal, and the third device may execute the computer program product, thereby performing the method according to embodiments in a distributed manner.

For example, the server (e.g., a cloud server, an artificial intelligence (AI) server, or the like) may execute the computer program product stored in the server, and may control the terminal to perform the method according to embodiments, the terminal communicating with the server.

As another example, the third device may execute the computer program product, and may control the terminal to perform the method according to embodiments, the terminal communicating with the third device. In more detail, the third device may remotely control the tomographic imaging apparatus to emit X-ray to an object, and to generate an image of an inner part of the object, based on detected radiation which passes the object and is detected in an X-ray detector.

As another example, the third device may execute the computer program product, and may directly perform the method according to embodiments, based on at least one value input from an auxiliary device (e.g., a gantry of CT system). In more detail, the auxiliary device may emit X-ray to an object and may obtain information of radiation which passes the object and is detected in an X-ray detector. The third device may receive an input of signal information about the detected radiation from the auxiliary device, and may generate an image of an inner part of the object, based on the input radiation information.

In a case where the third device executes the computer program product, the third device may download the computer program product from the server, and may execute the downloaded computer program product. Alternatively, the third device may execute the computer program product that is pre-loaded therein, and may perform the method according to the embodiments.

According to one or more embodiments, a tomographic imaging apparatus using a PCD in which a high counting speed and energy spectrum accuracy are simultaneously obtained, a method of controlling the tomographic imaging apparatus, and a computer program product are provided.

Also, according to one or more embodiments, a photon counting speed may be increased while reducing a dead time of photon counting by complementing advantages of using an energy spectrum method having excellent energy resolution and using a high speed counting method having a high photon counting speed in a PCD.

Although the present disclosure has been described with various embodiments, various changes and modifications may be suggested to one skilled in the art. It is intended that the present disclosure encompass such changes and modifications as fall within the scope of the appended claims.

What is claimed is:

1. A tomographic imaging apparatus comprising:
   an X-ray detector comprising a plurality of dual mode pixels and configured to detect radiation that has passed through an object; and
   at least one processor configured to obtain scan data from the X-ray detector, and control each pixel of the plurality of dual mode pixels to operate in one of a first mode and a second mode,
   wherein each pixel of the plurality of dual mode pixels comprises:
      a sensor configured to generate a scan signal by converting incident radiation into an electric signal;
      a first signal path circuit configured to transmit the scan signal in the first mode;
      a second signal path circuit configured to transmit the scan signal in the second mode; and
      a photon counter configured to count photons from the scan signal transmitted through one of the first and second signal path circuits,
   wherein a minimum time interval of transmitting the scan signal of the second signal path circuit is smaller than that of the first signal path circuit.

2. The tomographic imaging apparatus of claim 1, wherein the first signal path circuit comprises:
   a first preamplifier configured to amplify the scan signal; and
   a pulse shaper configured to shape a waveform of the scan signal.

3. The tomographic imaging apparatus of claim 1, wherein the second signal path circuit comprises:
   a second preamplifier configured to amplify the scan signal; and
   a reset circuit configured to reset input and output levels of the second preamplifier when the output level of the second preamplifier exceeds a first level.

4. The tomographic imaging apparatus of claim 1, wherein the at least one processor is further configured to generate a model selection signal for selecting one of the first mode and the second mode and output the mode selection signal to the X-ray detector, wherein each of the plurality of dual mode pixels further comprises:
   a first switch configured to transmit, to one of the first signal path circuit and the second signal path circuit, the scan signal output from the sensor, according to the mode selection signal; and
   a second switch configured to connect, to one of the first signal path circuit and the second signal path circuit, an input terminal of the photon counter, according to the mode selection signal.

5. The tomographic imaging apparatus of claim 1, wherein the X-ray detector comprises a plurality of binning pixels comprising a plurality of sub-pixels, wherein the plurality of dual mode pixels are grouped as sub-pixels to be included in the plurality of binning pixels, and
   the at least one processor is further configured to control at least one first dual mode pixel in each of the plurality of binning pixels to operate in the first mode and control remaining at least one second dual mode pixel excluding the at least one first dual mode pixel to operate in the second mode.

6. The tomographic imaging apparatus of claim 1, wherein the X-ray detector further comprises an anti-scatter grid provided on the plurality of dual mode pixels, and
   the at least one processor is further configured to control, from among the plurality of dual mode pixels, dual mode pixels provided around a frame of the anti-scatter grid to operate in the first mode and control remaining dual mode pixels excluding the dual mode pixels provided around the frame to operate in the second mode.

7. The tomographic imaging apparatus of claim 1, wherein the at least one processor is further configured to control, from among the plurality of dual mode pixels, dual mode pixels provided at an outer region to operate in the first mode and control remaining dual mode pixels excluding the dual mode pixels provided at the outer region to operate in the second mode.

8. The tomographic imaging apparatus of claim 1, further comprising an input device configured to receive a first control signal, wherein the at least one processor is further configured to control a mode of each of the plurality of dual mode pixels of the X-ray detector based on the first control signal.

9. The tomographic imaging apparatus of claim 1, further comprising an X-ray generator configured to generate and output X-rays,
  wherein the at least one processor is further configured to control a mode of each of the plurality of dual mode pixels based on at least one of a tube voltage and a tube current of the X-ray generator.

10. The tomographic imaging apparatus of claim 1, wherein the at least one processor controls a mode of each of the plurality of dual mode pixels based on an imaging protocol.

11. The tomographic imaging apparatus of claim 1, wherein the photon counter comprises:
  a plurality of comparators configured to compare the scan signal transmitted via one of the first signal path circuit and the second signal path circuit with a threshold voltage; and
  a plurality of counters respectively configured to count output signals of the plurality of comparators.

12. A method of controlling a tomographic imaging apparatus, wherein an X-ray detector of the tomographic imaging apparatus comprises a plurality of dual mode pixels operating in a first mode or a second mode, wherein each pixel of the plurality of dual mode pixels comprises a first signal path circuit configured to transmit a scan signal output from a sensor in the first mode, a second signal path circuit configured to transmit the scan signal in the second mode, and a photon counter configured to count photons from the scan signal, the method comprising:
  controlling each pixel of the plurality of dual mode pixels to operate in one of the first mode and the second mode; and
  obtaining scan data output from the X-ray detector, wherein a minimum time interval of transmitting the scan signal of the second signal path circuit is smaller than that of the first signal path circuit.

13. The method of claim 12, further comprising:
  shaping, by a pulse shaper included in the first signal path circuit, a waveform of the scan signal, in the first mode; and
  resetting, by a reset circuit included in the second signal path circuit, input and output levels of a second pre-amplifier of the second signal path circuit when the output level of the second preamplifier exceeds a first level, in the second mode.

14. The method of claim 12, wherein the plurality of dual mode pixels are grouped as sub-pixels and included in a plurality of binning pixels, and
  the method further comprises:
    controlling at least one first dual mode pixel in each of the plurality of binning pixels to operate in the first mode; and
    controlling remaining at least one second dual mode pixel excluding the at least one first dual mode pixel to operate in the second mode.

15. The method of claim 12, wherein the X-ray detector further comprises an anti-scatter grid provided on the plurality of dual mode pixels, and
  the method further comprises:
    controlling, from among the plurality of dual mode pixels, dual mode pixels provided around a frame of the anti-scatter grid to operate in the first mode; and
    controlling remaining dual mode pixels excluding the dual mode pixels provided around the frame to operate in the second mode.

16. The method of claim 12, further comprising:
  controlling, from among the plurality of dual mode pixels, dual mode pixels provided at an outer region to operate in the first mode; and
  controlling remaining dual mode pixels excluding the dual mode pixels provided at the outer region to operate in the second mode.

17. The method of claim 12, further comprising:
  receiving a first control signal; and
  controlling a mode of each of the plurality of dual mode pixels based on the first control signal.

18. The method of claim 12, further comprising controlling a mode of each of the plurality of dual mode pixels based on at least one of a tube voltage and a tube current of an X-ray generator.

19. The method of claim 12, further comprising controlling a mode of each of the plurality of dual mode pixels based on an imaging protocol.

20. A computer program product comprising a computer-readable recording medium having recorded thereon a program which, when executed by a processor, causes a tomographic imaging apparatus comprising an X-ray detector, the X-ray detector comprising a plurality of dual mode pixels operating in a first mode or a second mode, wherein each pixel of the plurality of dual mode pixels comprises a first signal path circuit configured to transmit a scan signal output from a sensor in the first mode, a second signal path circuit configured to transmit the scan signal in the second mode, and a photon counter configured to count photons from the scan signal to:
  control each pixel of the plurality of dual mode pixels to operate in one of the first mode and the second mode;
  obtain scan data output from the X-ray detector, wherein a minimum time interval of transmitting the scan signal of the second signal path circuit is smaller than that of the first signal path circuit.

* * * * *

UNITED STATES PATENT AND TRADEMARK OFFICE
CERTIFICATE OF CORRECTION

PATENT NO. : 10,713,822 B2
APPLICATION NO. : 16/147378
DATED : July 14, 2020
INVENTOR(S) : Sang-min Lee et al.

Page 1 of 1

It is certified that error appears in the above-identified patent and that said Letters Patent is hereby corrected as shown below:

In the Claims

Column 24, Claim 3, Line 17, delete "input and output levels" and insert --input level and output level--
Column 24, Claim 4, Line 22, delete "a model" and insert --a mode--
Column 25, Claim 13, Line 42, delete "input and output levels" and insert --input level and output level--

Signed and Sealed this
Sixth Day of October, 2020

Andrei Iancu
*Director of the United States Patent and Trademark Office*